United States Patent [19]

Stanley et al.

[11] Patent Number: 5,360,939

[45] Date of Patent: Nov. 1, 1994

[54] HOMOGENEOUS BIMETALLIC HYDROFORMYLATION CATALYSTS, AND PROCESSES UTILIZING THESE CATALYSTS FOR CONDUCTING HYDROFORMYLATION REACTIONS

[75] Inventors: George G. Stanley, Baton Rouge, La.; Scott A. Laneman, Vernon Hills, Ill.

[73] Assignee: Board of Supervisors of Louisiana State University and Agricultural and Mechanical College, Baton Rouge, La.

[21] Appl. No.: 180,537

[22] Filed: Jan. 12, 1994

Related U.S. Application Data

[60] Continuation of Ser. No. 28,415, Mar. 9, 1993, which is a division of Ser. No. 573,355, Aug. 27, 1990, Pat. No. 5,200,539.

[51] Int. Cl.$^5$ .................. C07C 45/50; C07F 15/00
[52] U.S. Cl. ..................... 568/454; 556/21; 556/23
[58] Field of Search ............. 556/21, 23; 568/451, 568/454

[56] References Cited

U.S. PATENT DOCUMENTS

| | | | |
|---|---|---|---|
| 3,939,188 | 2/1976 | McVicker | 260/429 |
| 4,987,242 | 1/1991 | Khanna et al. | 556/21 X |
| 5,200,539 | 4/1993 | Stanley et al. | 556/21 |

OTHER PUBLICATIONS

Laneman et al., Synthesis of a Binucleating Tetratertiary Phosphine Ligand System and the Structural Characterization of both Meso and Racemic Diastereomers of $Ni_2Cl_4$ (eLTTP) (eLTTP=$(Et_2PCH_2CH_2)(Ph)PCH_2P(Ph)(CH_2CH_2PEt_2)$), Inorganic Chem., vol. 28, pp. 1872–1878 (1989).

Stanley, "Novel Bimetallic Complexes Based on Binucleating Polyphosphine Ligands," NSF Grant Proposal submitted Sep. 23, 1988.

Laneman et al., A New Class of Binucleating Tetratertiaryphosphine Ligands. The Synthesis and Crystallographic Characterization of the Chiral Diastereomer of a Rhodium(I) Dimer: $RH_2Cl_2(CO)_2$(eLTTP) (eLTTP=$(Et_2PCH_2CH_2)(Ph)PCH_2P(Ph)(CH_2CH_2PEt_2)$), J. Amer. Chem. Soc., vol. 110, pp. 5585–5586 (1988).

*Primary Examiner*—Werren B. Lone
*Attorney, Agent, or Firm*—Llewellyn A. Proctor; John H. Runnels

[57] ABSTRACT

Novel homogeneous bimetallic hydroformylation catalysts, and processes utilizing these catalysts to convert alkenes, particularly alpha olefins, under mild conditions to a product rich in aldehydes, particularly a product containing a high ratio of linear:branched chain aldehydes. The catalysts can be produced from a binucleating tetratertiaryphosphine ligand capable of strongly coordinating two metal centers and holding them in general proximity to one another. Bimetallic catalyst precursors are produced which, on reaction with carbon monoxide and hydrogen, form the active bimetallic hydroformylation catalyst system.

9 Claims, No Drawings

HOMOGENEOUS BIMETALLIC HYDROFORMYLATION CATALYSTS, AND PROCESSES UTILIZING THESE CATALYSTS FOR CONDUCTING HYDROFORMYLATION REACTIONS

PRIOR APPLICATION

This application is a continuation of copending application Ser. No. 08/028,415, filed Mar. 9, 1993, which in turn is a divisional of U.S. patent application Ser. No. 07/573,355, filed Aug. 27, 1990, U.S. Pat. No. 5,200,539 the entire disclosure of which is incorporated by reference.

FIELD OF THE INVENTION

This invention relates to novel homogeneous hydroformylation catalysts, and processes for the use of such catalysts in conducing hydroformylation reactions. In particular, it relates to novel bimetallic catalyst complexes which selectively convert alkenes to linear aldehydes when a feed constituted of alkenes, hydrogen and carbon monoxide is reacted in the presence of said catalyst complexes.

BACKGROUND

Hydroformylation, earlier termed the oxo reaction, is an established process used by the chemical industry for converting alkenes to aldehydes, and sometimes alcohols, by reaction with hydrogen and carbon monoxide. Typically a feed stream constituted of alkenes, hydrogen and carbon monoxide is reacted over soluble rhodium- or cobalt-based transition metal catalysts at relatively low temperatures and pressures. Rhodium catalysts, the catalysts of choice for hydroformylation reactions, have long been recognized as more active than cobalt for promoting the "oxo" reaction, especially at low temperatures and pressures, even when the catalyst is used in relatively low concentrations. Rhodium catalysts, which produce primarily aldehydes, have also provided generally good selectivities in the production of linear aldehydes. Rhodium catalysts, however, require, inter alia, the use of an excess of a phosphine ligand in the reaction to stabilize the catalyst against the formation of decomposition products, and to maintain acceptably high product selectivities.

In U.S. Pat. No. 3,939,188 to Gary B. McVicker there is disclosed a laundry list of complex zero-valent rhodium catalysts useful for conducting hydroformylation reactions. These catalysts are represented by the formulae $[(L)(L')Rh^0]_2$, $[(L_3)Rh^0]_2$, $[L'_2Rh^0]_2$, $[(L'')Rh^0]_2$, where L is a monodentate ligand, L' is a bidentate ligand, and L'' is a tri- or quadradentate ligand, wherein L, L', and L'' can be the same or different and each one is selected from the group consisting of:

1. $R_3Q$, $R_2R'Q$, $(RR'R'')Q$
2. $R_2Q(CR_2')_xQ'R_2$
3. $R_2Q(CR_2')Q'(R'')(CR_2')_xQR_2$
4. $R_2Q'(CR_2')_xQ(R'')(CR_2')_xQ(R'')(CR_2')_xQ'R_2$
5. $RQ'[(CR_2')_xQR_2]_2$
6. $Q'[(CR_2')_xQR_2]_3$ wherein R, R', and R'' can be the same or different and each is selected from the group consisting of hydrogen, F, Cl, Br, and I, $C_1$ to $C_{20}$ alkyl, $C_1$ to $C_{20}$ alkoxy, $C_3$ to $C_8$ cycloalkyl, $C_3$ to $C_8$ cycloalkoxy, phenyl, phenyl substituted with F, Cl, Br, and I, phenyl substituted with $C_1$ to $C_{20}$ alkyl, phenyl substituted with $C_3$ to $C_8$ cycloalkyl, phenyl substituted with $C_1$ to $C_{20}$ alkoxy, oxyphenyl, oxyphenyl substituted with $C_3$ to $C_8$ cycloalkyl, oxyphenyl substituted with F, Cl, Br, and I, oxyphenyl substituted with $C_3$ to $C_8$ cycloalkoxy; Q and Q' can be the same or different and each is selected from the group consisting of P, As, Sb, and x is an integer ranging from 1 to 5.

These catalysts were prepared in accordance with one or the other of the following reactions:

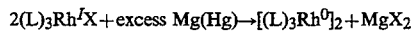

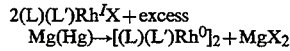

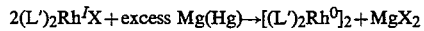

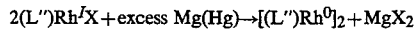

X=Cl, Br, I, F; preferably Cl, Br, or I

The reduction of the rhodium(I) complex is performed in an inert atmosphere, at low to moderate temperature and pressure, with an excess of magnesium amalgam in the presence of solvent.

These catalysts, like other homogeneous catalyst systems employed for hydroformylation reactions, require the use of an excess of phosphine ligand to stabilize the catalyst, suppress decomposition reactions, and maintain acceptable selectivities. Better stability, particularly better stability without the use of an excess of a phosphine ligand, and improved selectivity in obtaining higher yields of the desired products are desired by the industry. Nonetheless, despite these shortcomings the $Rh/PPh_3$ catalyst system continues in wide use throughout the chemical industry.

OBJECTS

It is, accordingly, a primary objective of this invention to provide novel catalyst compositions of high activity and selectivity in carrying out hydroformylation reactions.

In particular, it is an object to provide a novel bimetallic hydroformylation catalyst, particularly a catalyst which is highly active, selective, and stable under hydroformylation reactions conditions and does not require the addition of excess phosphine ligand to the reaction when conducting a hydroformylation reaction.

A further, and more specific object is to provide novel homogeneous bimetallic hydroformylation catalyst compositions, particularly rhodium- and ruthenium-based hydroformylation catalyst compositions, and processes using these catalysts in conducting hydroformylation reactions to produce products rich in both linear and branched aldehydes; but particularly selective in producing products rich in linear aldehydes.

STATEMENT OF INVENTION

These objects and others are achieved in accordance with this invention through catalyst compositions, and processes using these compositions in conducting hydroformylation reactions, with catalysts characterized structurally by formula (I) as follows:

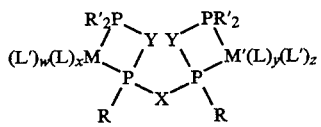

(I)

wherein M and M' can be the same or different, and each is a Group VIII metal of the Periodic Table of the Elements (E. H. Sargent & Co. Scientific Laboratory Equipment, copyright 1962), preferably a metal selected from the group consisting of rhodium, ruthenium, cobalt, iron and palladium, or a Group IB metal, preferably copper; X is selected from the group consisting of methylene, substituted methylene $CR^1R^2$ where $R^1$ and $R^2$ can be the same or different and each consists of a hydrocarbon moiety which can be saturated or unsaturated and contains up to 20 carbon atoms and is a $C_1$ to $C_5$ alkyl (e.g., methyl, ethyl, n-butyl), $C_2$ to $C_5$ alkyenyl (e.g., vinyl, allyl, 1-butenyl), $C_1$ to $C_5$ alkoxy (e.g., methoxy, ethyoxy, butoxy), $C_1$ to $C_{20}$ alcohol (e.g., $-CH_2OH$, $-CH_2CH_2OH$), $C_3$ to $C_6$ cycloalkyl (e.g., cyclopropyl, cyclopentyl), $C_3$ to $C_6$ cycloalkyoxy (e.g., cyclopropoxy, cyclopentoxy), $C_6$ to $C_{10}$ aryl (e.g., phenyl, naphthyl), $C_6$ to $C_{10}$ alkaryl (e.g., tolyl, xylyl), $C_6$ to $C_{10}$ aralkyl (e.g., benzyl, betaphenylethyl), or the like, and preferably X is methylene, oxygen, $NR^3$ where $R^3$ is a hydrocarbon moiety which can be saturated or unsaturated and contains up to 20 carbon atoms and is a $C_1$ to $C_5$ alkyl (e.g., methyl, ethyl, n-butyl), $C_2$ to $C_5$ alkyenyl (e.g., vinyl, allyl, 1-butenyl), $C_1$ to $C_5$ alkoxy (e.g., methoxy, ethyoxy, butoxy), $C_1$ to $C_{20}$ alcohol (e.g., $-CH_2OH$, $-CH_2CH_2OH$), $C_3$ to $C_6$ cycloalkyl (e.g., cyclopropyl, cyclopentyl), $C_3$ to $C_6$ cycloalkoxy (e.g., cyclopropoxy, cyclopentoxy), $C_6$ to $C_{10}$ aryl (e.g., phenyl, naphthyl), $C_6$ to $C_{10}$ alkaryl (e.g., tolyl, xylyl), $C_6$ to $C_{10}$ aralkyl (e.g., benzyl, betaphenylethyl), or the like, and preferably X is methylene; Y is an ethyl, propyl, or meta-substituted aryl linkage with hydrogen, F, or methyl substituents, and, preferably Y is an ethyl group; R is a hydrocarbon moiety which can be saturated or unsaturated and contains up to 20 carbon atoms and is a $C_1$ to $C_{20}$ alkyl (e.g., methyl, ethyl, n-butyl, iso-propyl), $C_1$ to $C_8$ alkoxy (e.g., methoxy, ethyoxy, butoxy), $C_1$ to $C_{20}$ alcohol (e.g., $-CH_2OH$, $-CH_2CH_2OH$), $C_3$ to $C_6$ cycloalkyl (e.g., cyclopropyl, cyclopentyl), $C_3$ to $C_6$ cycloalkyoxy (e.g., cyclopropoxy, cyclopentoxy), $C_6$ to $C_{10}$ aryl (e.g., phenyl, naphthyl), $C_6$ to $C_{10}$ alkaryl (e.g., tolyl, xylyl), $C_6$ to $C_{10}$ aralkyl (e.g., benzyl, betaphenylethyl), or the like, and preferably R is an aryl, suitably phenyl; R' is a hydrocarbon moiety which can be saturated or unsaturated and contains up to 20 carbon atoms and is a $C_1$ to $C_{20}$ alkyl (e.g., methyl, ethyl, n-propyl, n-butyl, iso-propyl), $C_1$ to $C_8$ alkoxy (e.g., methoxy, ethyoxy, propoxy, butoxy), $C_1$ to $C_{20}$ alcohols (e.g., $-CH_2OH$, $-CH_2CH_2OH$), $C_3$ to $C_6$ cycloalkyl (e.g., cyclopropyl, cyclopentyl), $C_3$ to $C_6$ cycloalkoxy (e.g., cyclopropoxy, cyclopentoxy), $C_6$ to $C_{10}$ aryl (e.g., phenyl, naphthyl), $C_6$ to $C_{10}$ alkaryl (e.g., tolyl, xylyl), $C_6$ to $C_{10}$ aralkyl (e.g., benzyl, betaphenylethyl), or the like, and preferably R' is an alkyl, suitably ethyl. The ligands L and L' attached to each of the metal atoms, M and M', can be the same or different and can be H, CO, alkene, alkyls, or other related ligands present either initially in the catalyst precursor or as form in situ during the hydroformylation reaction.

The bimetallic hydroformylation catalyst composition embodied by formula (I) can be written in a more simplified form as (IA):

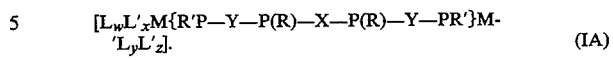

(IA)

The catalyst embodied by formula I or IA is formed by reaction between the polyphosphine ligand characterized by formula II, hereinafter LTTP,

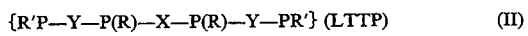 (LTTP)  (II)

as follows: LTTP and two molecules of a metal complex capable of complexing with the LTTP ligand form a generalized bimetallic complex characterized by formula III, as follows:

 (III)

wherein M and M' can be the same or different, L and L' can be the same or different and are ancillary ligands such as hydrogen, halogen, carbonyl, norbornadiene, or the like. The charge on complex III will depend on the oxidation state of the metal centers and the charges and respective numbers of the ligands L and L' designated by w, x, y and z. The values of the numbers w, x, y and z for the ligands L and L' are related to the exact nature of the metal centers and are set to give 14, 16, or 18 electron metal valence electron counts. For example, in the case of $M=M'=$rhodium, $L=H$, $L'=CO$, $w=y=1$, and $x=z=1$.

LTTP, the ligand represented by formula II, acts as a template for building the bimetallic metal complex, and has the ability to both bridge and chelate two metal centers, each of which will lie near the geometric center of the complex in general proximity to one another. LTTP is thus preferably a binucleating tetratertiaryphosphine ligand having a bridging-chelating framework open at its center at which reaction with two metal centers can occur to produce bischelated bimetallic complexes represented by formula III. A preferred LTTP is one wherein the internal phosphorus atoms are linked through a methylene bridge, Y is an ethyl linkage, R is phenyl or a low molecular weight alkyl, and R' is a low molecular weight alkyl, such as ethyl (Et), as represented by the following structural formula:

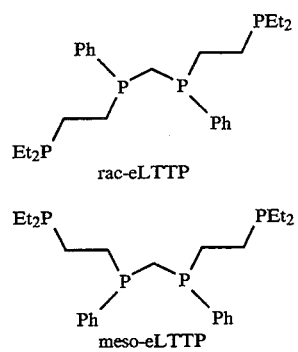

A tetratertiaryphosphine of this type is chiral at the two internal phosphorus atoms, resulting in both racemic (R,R; S,S) and meso (R,S) diastereomers, a potentially desirable feature in promoting potential stereo- and enantio-selective reactions.

The catalyst of this invention is highly active and can convert alkenes, notably alpha olefins, via hydroformylation to linear and branched aldehydes at fast rates with remarkably high selectivities ($\approx 30:1$ linear to branched). Unlike present commercially used catalysts there is no need to add excess phosphines to the reaction mixture to maintain the stability of the catalyst. The reason the catalysts of this invention produce a product having a high linear:branched aldehyde product ratio, it is believed, is due to the geometric configuration of the $M_2$(LTTP) moiety. When, for example, an alkene coordinates to $Rh_2H_2(CO)_2$(LTTP) it can only add to one of the outside axial rhodium coordination sites. As the olefin coordinates to the rhodium center, the other ligands tend to bend away, ideally to form a trigonal bipyramid or square pyramid which is the least sterically hindered geometry for a 5-coordinate rhodium complex. $Rh_2$(LTTP), however, can not attain this geometry because the other haft of the complex is present and limits the extent of ligand motion toward trigonal bipyramidal or square pyramidal. By minimizing the geometry reorganization about the metal center, the steric effects are maximized and the alkene insertion into the M—H bond is directed toward the anti-Markovnikov alkene position to form a linear alkyl group which is then converted into the linear aldehyde product.

The considerable activity of this bimetallic LTTP-based catalyst system is also most unusual since it is well known that electron-rich phosphine ligands generally inhibit the activity and selectivity of Rh-based hydroformylation catalysts. We believe that the dramatic rate enhancement observed in the $Rh_2H_2(CO)_2$(LTTP) catalyst system is due to bimetallic cooperativity, specifically, an intramolecular hydride transfer from one metal center to the other. The rotational flexibility of $Rh_2$(LTTP) has been probed by performing van der Waals (VDW) energy calculations on the model complex $Rh_2H_2(CO)_2$(LTTP). The molecular modeling calculations show that $Rh_2H_2(CO)_2$(LTTP) should have a considerable amount of conformational flexibility. Most importantly, the VDW calculation indicates that this complex can readily access a closed-mode orientation in which the two Rh centers approach one another. This rotational flexibility is significant because square-planar complexes based on the more sterically hindered binucleating hexaphosphine ligand $(Et_2PCH_2CH_2)_2PCH_2P(CH_2CH_2PEt_2)_2$ which we have also studied (Cf., Askham, F. A.; Marques, E. C.; Stanley, G. G. *J. Am. Chem. Soc.* 1985, 107, 3082; Laneman, S. A.; Stanley, G. G. *Inorg. Chem.* 1987, 26, 1177; Saum, S. E.; Stanley, G. G. *Polyhedron* 1987, 6, 1803; Saum, S. E.; Askham, F. R.; Fronczek, F.; Stanley, G. G. *Organometallics* 1988, 7, 1409; Saum, S. E.; Laneman, S. A.; Stanley, G. G. *Inorg. Chem.* 1991, 30 in press) cannot form closed-mode complexes due to severely unfavorable intramolecular steric interactions. Similarly bimetallic bis(diphenylphosphino)-methane (dppm) A-frame complexes of rhodium, $Rh_2$(dppm)$_2$, are terrible hydroformylation catalysts because they lack the rotational flexibility found in $Rh_2$(LTTP) (Cf. Sanger, A. R. *Homogeneous Catalysis with Metal Phosphine Complexes* Pignolet, L. H. (ed.); Plenum; New York, 1983; pp 215–237.).

The VDW energy molecular modelling studies clearly support the premise that the two rhodium atoms in $Rh_2H_2(CO)_2$(LTTP) can approach one another and have the proper geometry for a facile hydride transfer from one Rh atom to another. In the hydroformylation catalytic cycle a species similar to $Rh(acyl)(CO(\mu\text{-}LTTP)RhH(CO)$ would be a key intermediate in the catalytic cycle and that this type of system could readily access a "closed-mode" conformation in which an intramolecular hydride transfer could occur. Such a proposed intermediate species is shown below.

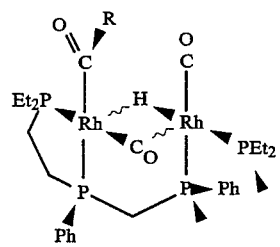

The $Rh_2$(LTTP) unit essentially acts as a conventional monometallic hydroformylation catalyst until it reaches the acyl intermediate. Then, the rotational flexibility of the LTTP ligand comes into play and bimetallic cooperativity takes place to transfer a hydride to the acyl-bound rhodium. Reductive elimination of aldehyde product, it is believed, will then generate a Rh—Rh bonded complex which can react with $H_2$ to regenerate the $Rh_2H_2(CO)_2$(LTTP) starting catalyst.

One of the unique features of the LTTP ligand system is that it is relatively straightforward to prepare monometallic analogs that incorporate "half" of the LTTP ligand. $Et_2PCH_2CH_2PEt_2$ (depe) $Et_2PCH_2CH_2PMePh$ (depmpe) and $Et_2PCH_2CH_2PPh_2$ (dedppe) ligands have been prepared to act as electronically similar monometallic model ligand systems. All these model monometallic [Rh(norbornadiene)]($P_2$)($BF_4$) hydroformylation catalysts turn out to have similarly poor activities and selectivities, as shown in Table A. This result is completely consistent with the well known deactivating effect of electron-rich phosphine ligands on Rh-based hydroformylation catalysts.

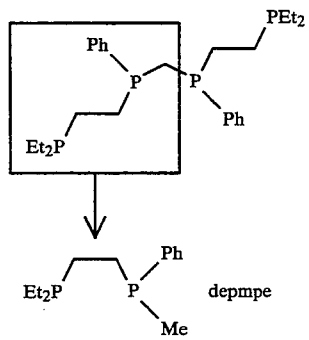

Rh(norb)(depmpe)+ is, perhaps, the most analogous monometallic complex to our bimetallic $Rh_2(norb)_2$(LTTP)$^{2+}$ system and is a very poor hydroformylation catalyst (see Table A). It has an initial turnover frequency of about 5/hr with a product aldehyde selectivity of only 2:1 linear to branched with large amounts of alkene isomerization observed. Our bimetallic LTTP-based catalyst system is, therefore, at least 70 times faster than this "electronically correct" monometallic analog and markedly more selective and effective as a hydroformylation catalyst system.

TABLE A

Comparison of Bimetallic Rh₂(LTTP) Catalyst with Mono- and Bi-Metallic Model Systems

| Catalyst* | Temp °C. | $H_2$ psig | CO psig | Initial 1-Hexene moles/L | Initial Rate TO/hr** | Linear/ Branched $C_7$ Aldehyde Mole Ratio | % Alkene Isomerization |
|---|---|---|---|---|---|---|---|
| $Rh_2(norb)_2(LTTP)^{2+}$ | 80 | 30 | 30 | 1.9 | 370 | 30 | 8 |
| $Rh(norb)(depe)^+$ | 80 | 30 | 30 | 1.9 | 45 | 3 | 50 |
| $Rh(norb)(depmpe)^+$ | 80 | 30 | 30 | 1.9 | 5 | 3 | 85 |
| $Rh(norb)(dedppe)^+$ | 80 | 30 | 30 | 1.9 | 4 | 3 | 85 |
| $Rh_2(norb)_2(LTTP-pr)^{2+}$ | 80 | 30 | 30 | 1.9 | 10 | 4 | 94 |
| $Rh_2(norb)_2(LTTP-p-xyl)^{2+}$ | 80 | 30 | 30 | 1.9 | 2 | 2 | 95 |

*Counter anion is $BF_4^-$
**Turnovers/hr, initial rate measured during first hour of operation on a per mole catalyst basis.

Bimetallic model systems have also been prepared which have "spacer" groups replacing the central methylene bridge to probe the importance of having two metal centers present and near one another. Bimetallic rhodium norbornadiene complexes based on p-xylene and propylene bridged tetraphosphine ligands (LTTP-p-xyl and LTTP-pr) shown below have been prepared and studied as hydroformylation catalysts.

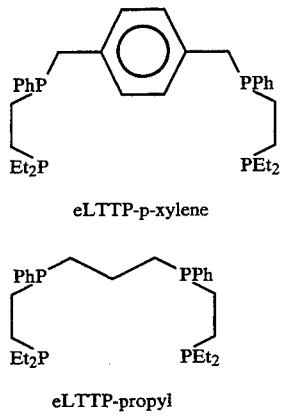

eLTTP-p-xylene eLTTP-propyl

Bimetallic Rh-norbornadiene complexes based on these spaced binucleating tetraphosphine ligands produce very poor hydroformylation catalysts giving results that essentially mirror those seen for the monometallic model systems. The hydroformylation catalytic results for the mono- and bi-metallic complexes discussed here are also summarized in Table A. Molecular modelling studies of the Rh₂H₂(CO)₂(LTTP-p-xylene) and Rh₂H₂(CO)₂(LTTP-propyl) catalyst systems clearly indicate that it will be very difficult, if not impossible for the metal centers in these systems to approach one another for an intramolecular hydride transfer. Thus, the presence of the single atom bridge in LTTP which constrains the two square planar rhodium centers to adopt a rotationally flexible face-to-face orientation may well be the key design feature in the Rh₂(LTTP) complex. This, once again, allows facile intramolecular hydride transfer between the metal centers, greatly enhancing the rate and efficiency of the hydroformylation reaction.

Techniques for the preparation of LTTP are described in the literature. e.g., Inorg. Chem. 1989, 28, 1872 by Laneman et al. The preparation described involves the building of the central bis(phosphino)methane unit by reaction of KP(H)Ph with $CH_2Cl_2$, and the treatment of the isolated Ph(H)PCH₂P(H)Ph species with two equivalents of $R_2P(HC=CH_2)$ under AIBN free-radical-catalyzed conditions to produce LTTP, e.g.:

Scheme I
eLTTP Synthesis

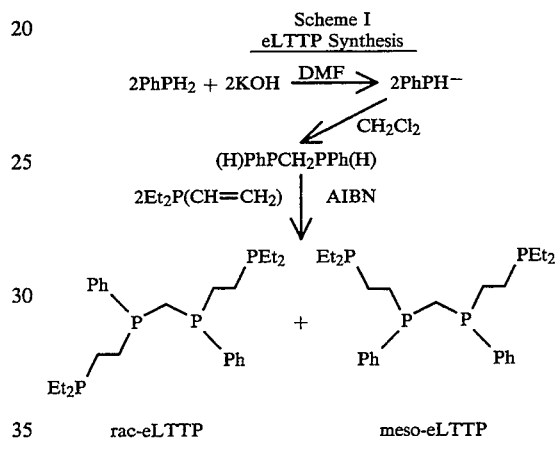

rac-eLTTP    meso-eLTTP

The ethylene-linked terminal phosphines in LTTP simplify the synthetic procedure and give higher yields of the final tetraphosphine (88–92%) based on Ph(H)PCH₂P(H)Ph, or 39–43% yields based on the starting PhPH₂. The presence of the phenyl groups on the central P—CH₂—P bridge allows more facile crystallizations of bimetallic complexes. The electron-rich alkylated terminal and mostly alkylated internal phosphines coordinate strongly with metal centers and provide a very effective means for inhibiting ligand dissociation and bimetallic fragmentation.

The meso and racemic diastereomers of LTTP are both highly reactive binucleating ligands that can bridge and chelate two metal centers, albeit each can form complexes that have different overall geometrical orientations of the phosphines about the two metal centers. The reaction of a metal compound as described by reference to formula III, however, will produce a large amount of the hydroformylation catalyst composition of the general geometrical configuration described by reference to formula I. For example, the reaction of [Rh(norbornadiene)₂](BF₄) with LTTP produced the bimetallic hydroformylation catalyst composition described by formula I wherein X=CH₂, Y=CH₂CH₂, R=phenyl/(Ph), R'=ethyl/(Et), L=L'=norbornadiene, and M=Rh, viz. [Rh₂(norbornadiene)₂(LTTP)](BF₄)₂ in 80–90% isolated yield; the first diastereomer of this complex to crystallize out of a tetrahydrofuran (THF) solution being the racemic-[Rh₂(norbornadiene)₂(LTTP)](BF₄)₂ complex. This complex has been characterized by ¹H and ³¹P NMR, elemental analysis, and single-crystal X-ray diffraction.

The process of this invention contemplates using these highly active bimetallic catalysts for converting alkenes to aldehydes, at high selectivity, by reacting the alkenes with the catalyst in a homogeneous reaction phase in the presence of carbon monoxide, CO, and hydrogen, $H_2$. The catalyst or catalyst precursor is introduced into the autoclave or reaction vessel dissolved in a liquid medium, or slurried, or otherwise dispersed in a liquid medium to eventually provide a homogeneous reaction phase. Suitable solvents are, e.g., alcohols, ethers, ketones, paraffins, cycloparaffins and aromatic hydrocarbons.

Feeds constituted of, or feeds containing alkenes such as alpha olefins, particularly straight chain alpha olefins, having from 2 to about 20 carbon atoms ($C_2$ to $C_{20}$), preferably from about $C_2$ to $C_{12}$, are preferred. The alpha olefins are characterized by a terminal double bond, i.e., $CH_2=CH-R$, and these groups may be substituted if the substituents do not interfere in the hydroformylation reactions. Exemplary of such substituents are carbonyl, carbonyloxy, oxy, hydroxy, alkoxy, phenyl and the like. Exemplary alpha olefins, or olefins unsaturated in the 1-position, include alkenes, alkyl alkenoates, alkenyl alkyl ethers, alkenols, and the like, e.g., ethylene, propene, 1-butene, 1-pentene, 1-hexene, 1-heptene, 1-octene, vinyl acetate, allyl alcohol, and the like.

The feed is contacted with the homogeneous catalyst, while carbon monoxide and hydrogen are added, at temperature, pressure and time sufficient to convert the alkene to aldehydes, at high selectivities. In general, the temperature of the reaction ranges from about 50° C. to about 150° C., preferably from about 60° C. to about 120° C. In general, total pressures range from about 20 pounds per square inch (psi) to about 300 psi, preferably from about 50 psi to about 200 psi. The ratio of $H_2$:CO ranges generally from about 10:90 to about 90:10 volume percent, preferably from about 40:60 to about 60:40 volume percent.

The catalyst is generally employed in the reaction mixture in concentrations ranging from about $10^{-5}$M to about $10^{-2}$M (molarity). The catalyst is added to the reaction vessel as a slurry or a solution, and the reaction is pressurized and brought to the desired operating temperature. The feed and the carbon monoxide and hydrogen in desired ratios are then introduced into the reaction vessel to commence an operation. Alkene feeds that are liquids at or near room temperature (e.g., 1-hexene, 1-octene) are introduced to the reaction zone prior to charging the $H_2$ and CO gases, although this is not a prerequisite for the reaction. The process is suited to batch-wise operation, or to continuous operation via the use of suitable apparatus.

The following examples, with comparative demonstrations, are further exemplary of the active and highly selective catalysts of this invention for use in conducting hydroformylation reactions. In the examples and demonstrations that follow, all parts are in terms of mole units, pressures in terms of pounds per square inch gauge, and temperatures expressed in terms of degrees Centigrade except as otherwise expressed.

In conducting this series of tests, it was found that the catalysts of this invention produce hydroformylation of the alkene feed under very mild conditions. Both linear and branched aldehyde are produced, but with remarkably high selectivity ratios of linear to branched aldehydes. This is done without any necessity of adding excess phosphine ligand to maintain catalyst stability and high product aldehyde selectivities. Virtually all current commercial $Rh/PR_3$ catalyst systems, in marked contrast, require excess phosphine ligand for stabilization of the $Rh/PR_3$ catalysts.

EXAMPLES

Catalyst Preparation

A binucleating tetratertiaryphosphine ligand $(Et_2CH_2CH_2)(Ph)PCH_2P(Ph)(CH_2CH_2PEt_2)$, was prepared by reacting two equivalents of $PhPH_2$ and one equivalent of $CH_2Cl_2$ with KOH in DMF solution to produce $Ph(H)PCH_2P(H)Ph$ which is isolated. $Ph(H)PCH_2P(H)Ph$ is then treated with two equivalents of $Et_2P(CH=CH_2)$ under AIBN free-radical-catalyzed conditions to produce $(Et_2CH_2CH_2)(Ph)PCH_2P(Ph)(CH_2CH_2PEt_2)$ in 88–92% isolated yield based on $Ph(H)PCH_2P(H)Ph$, or 39–43% yields based on the starting $PhPH_2$. All manipulations were carried out under inert atmosphere conditions in dried degassed solvents.

One equivalent of $(Et_2CH_2CH_2)(Ph)PCH_2P(Ph)(CH_2CH_2PEt_2)$ was then reacted with two equivalents of $[Rh(norbornadiene)_2](BF_4)$ in THF under inert atmosphere conditions to produce the bimetallic Rh(I) catalyst precursor $[Rh_2(norbornadiene)_2\{(Et_2CH_2CH_2)(Ph)PCH_2P(Ph)(CH_2CH_2PEt_2)\}](BF_4)_2$, hereafter $[Rh_2(norbornadiene)_2)LTTP)]^{2+}$, in essentially quantitative yield.

EXAMPLE 1

Hydroformylation of 1-Hexene

All operations were carried out under inert atmosphere conditions. 0.02 g (0.0195 mmol) of the $[Rh_2(norb)_2(LTTP)](BF_4)_2$ catalyst precursor was dissolved in 45 mL of acetone. 7.5 g (89.3 mmol) of 1-hexene was added and the mixture transferred to a 450 mL Parr stainless steel autoclave system. The autoclave is equipped with a packless magnetic drive stirring system and designed to introduce the gas mixture through a dip tube directly into the solution. Turbine type impellers and glass liners with built in baffles are used to obtain optimum solution/gas mixing. Stir rates of 1000–1200 rpm are typically used. The autoclave was also equipped with a pressure transducer for monitoring the pressure of the autoclave and a thermocouple for determining the temperature of the reaction mixture in the autoclave.

All runs were done under constant pressure conditions of $H_2$/CO. A 1:1 mixture of $H_2$/CO was then added to give an autoclave pressure of 30 psi. The temperature of the autoclave was increased to and stabilized at 80° C. (this took $\approx$10 min). The pressure in the autoclave was then levelled off at 80 psi for the duration of the run. Small aliquots (<1 mL) of the reaction mixture were typically taken for product analysis at regular intervals throughout the runs, which typically were left to run for 6 to 18 hours.

Rate data was obtained by monitoring the decrease in pressure of a 1 L reservoir cylinder that contained approximately 750 psi of $H_2$/CO which was delivered to the autoclave at constant pressure by a two-stage gas regulator. The pressure of the reservoir cylinder was constantly monitored by a pressure transducer. The reservoir pressure and temperature, autoclave temperature, and stir rate data were collected and stored on a Parr 4851 controller and the data transferred periodically to a PC computer for permanent storage and for calculating reaction rates. Analysis of products was performed by GC, NMR and GC/MS measurements.

Analyses of the product mixtures showed that 1-hexene was very cleanly hydroformylated to the linear and branched aldehydes 1-heptanal and 2-methyl-hexanal in a 30:1 linear to branched ratio. No alcohol or alkane formation was observed that amounted to over 1% of the product mixture. The data from this run is shown in Table 1 and is compared to a commercial $Rh/PPh_3$ catalyst system.

TABLE 1

Hydroformylation of 1-Hexene

| Catalyst[a] | P/Rh[b] | Temp °C. | $H_2$ psig | CO psig | Initial 1-Hexene moles/L | Initial Rate TO/hr[c] | Linear/ Branched $C_7$ Aldehyde Mole Ratio |
|---|---|---|---|---|---|---|---|
| $Rh_2(norb)_2(LTTP)^{2+}$ | 0.5 | 80 | 30 | 30 | 1.9 | 370 | 30 |
| $HRh(CO)(PPh_3)_3$ | 950 | 80 | 30 | 30 | 1.9 | 447.5 | 14 |

[a]Counter anion is $BF_4^-$ for cationic species
[b]Phosphine ligand to Rh molar ratio
[c]Turnovers/hr, initial rate measured during first hour of operation on a per mole catalyst basis.

The activity of the mixture of racemic and meso bimetallic $Rh_2(LTTP)$ catalysts is only 16% slower than that of the $Rh/PPh_3$ catalyst system which is used commercially on a large scale. This is most surprising since electron-rich phosphine ligands (either monodentate or polydentate) such as ours are well known to make rhodium centers far less active towards hydroformylation catalysis. Virtually all effective rhodium-phosphine-based hydroformylation catalyst systems use more electron deficient phosphine ligands such as $PPh_3$ (or substituted versions thereof) and $P(OR)_3$ (or substituted versions thereof). It is also known that electron-rich phosphine ligands generally cause decreases in product selectivities. For these reasons electron-rich phosphine ligands have proven to be very, poor ligands for rhodium hydroformylation catalysts.

In marked contract, however, the bimetallic LTTP-based dirhodium catalyst of this invention has both high activities and very high selectivities, giving an initial rate of 370 turnovers/hr and a linear to branched aldehyde product ratio of at least 30:1. Furthermore, because of the strong rhodium coordinating abilities of this electron-rich LTTP ligand system, an excess of phosphine ligand is not required either for catalyst stability or to enhance linear aldehyde production.

EXAMPLE 2

Hydroformylation of 1-Octene

All operations were carded out under inert atmosphere conditions. 0.02 g (0.0195 mmol) of the $[Rh_2(norb)_2(LTTP)](BF_4)_2$ catalyst precursor was dissolved in 42 mL of acetone. 7.55 g (67.3 mmol) of 1-octene was added and the mixture transferred to a 450 mL Parr autoclave system. The same autoclave system and methods of product analysis as described in Example 1 were used here.

Analyses of the product mixtures showed that 1-octene was very cleanly hydroformylated to the linear and branched aldehydes 1-nonanal and 2-methyl-octanal in a 23:1 linear to branched ratio. The data from this run is shown in Table 2.

TABLE 2

Hydroformylation of 1-Octene

| Catalyst[a] | Temp °C. | $H_2$ psig | CO psig | Initial 1-Octene moles/L | Initial Rate TO/hr[b] | Linear/Branched Aldehyde Mole Ratio |
|---|---|---|---|---|---|---|
| $Rh_2(norb)_2(LTTP)^{2+}$ | 80 | 30 | 30 | 1.3 | 217.5 | 23 |

[a]Counter anion is $BF_4^-$
[b]Turnovers/hr, initial rate measured during first hour of operation on a per mole catalyst basis.

EXAMPLE 3

Hydroformylation of Allyl Alcohol

All operations were carried out under inert atmosphere conditions. 0.02 g (0.0195 mmol) of the $[Rh_2(norb)_2(LTTP)](BF_4)_2$ catalyst precursor was dissolved in 42 mL of acetone. 7.75 g (134 mmol) of allyl alcohol was added and the mixture transferred to a 450 mL Parr autoclave system. The same autoclave system and methods of product analysis as described in Example 1 were used here.

Analyses of the product mixtures showed that allyl alcohol was very cleanly hydroformylated to the linear and branched aldehydes, 4-hydroxybutanal and 3-hydroxy-2-methyl-propanal, in greater than 30:1 linear to branched ratio; The data from this run is shown in Table 3.

TABLE 3

Hydroformylation of Allyl Alcohol

| Catalyst[a] | Temp °C. | $H_2$ psig | CO psig | Initial Allyl Alcohol moles/L | Initial Rate TO/hr[b] | Linear/Branched Aldehyde Mole Ratio |
|---|---|---|---|---|---|---|
| $Rh_2(norb)_2(LTTP)^{2+}$ | 80 | 30 | 30 | 2.8 | 654.5 | >30 |
| $Rh_2(norb)_2(LTTP)^{2+}$ | 90 | 30 | 30 | 2.8 | 797.5 | >30 |

[a]Counter anion is $BF_4^-$ for cationic species
[b]Turnovers/hr, initial rate measured during first hour of operation on a per mole catalyst basis.

It is apparent that various modifications and changes can be made without departing from the spirit and scope of the present invention.

We claim:

1. A process for converting an alkene or substituted alkene to a product rich in aldehydes at a high linear:-branched chain aldehyde ratio, which comprises contacting the alkene or substituted alkene, in the presence of carbon monoxide and hydrogen at conditions conducive to hydroformylation, with a composition comprising:

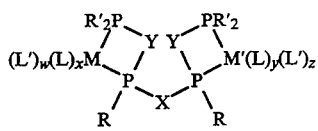

(I)

wherein

M is a Group VIII metal or Group IB metal;

M' is a Group VIII metal or Group IB metal;

X is selected from the group consisting of methylene; substituted methylene CSS' where S and S' can be the same or different, and each of S and S' is a hydrocarbon moiety which can be saturated or unsaturated and which contains up to 20 carbon atoms; oxygen; and NQ where Q is a hydrocarbon moiety which can be saturated or unsaturated and which contains up to 20 carbon atoms;

each Y is selected from the group consisting of ethyl; propyl; and meta-substituted aryl having hydrogen, F, or methyl substituents; where the Ys may be the same or different;

each R is a hydrocarbon moiety which can be saturated or unsaturated and which contains up to 20 carbon atoms; where the Rs may be the same or different;

each R' is selected from the group consisting of methyl, ethyl, n-propyl, n-butyl, methoxy, ethoxy, propoxy, and butoxy; where the R's may be the same or different;

each L and L' is a substituent ligand selected from the group consisting of H, CO, alkenyl, alkyl, substituted alkenyl, and substituted alkyl; where the Ls may be the same or different; and where the L's may be the same or different;

and the values of the numbers w, x, y, and z for the ligands L and L' depend on the metal centers M and M' and are selected such that each metal center M and M' has 14, 16, or 18 valence electrons.

2. The process of claim 1 wherein M and M' are each rhodium; X is methylene; Y is ethyl; each R is phenyl; and each R' is ethyl.

3. The process of claim 2, wherein each L' is CO, and wherein each of the numbers w, x, y, and z is 1.

4. The process of claim 1 wherein the composition is dispersed in a liquid medium to provide a homogeneous reaction phase.

5. The process of claim 1 wherein the alkene comprises alkenes, or substituted alkenes, having from 2 to about 20 carbon atoms.

6. The process of claim 1 wherein the composition is dispersed in a liquid medium to provide a homogeneous reaction phase, and the alkene or substituted alkene is contacted with the composition while the carbon monoxide and hydrogen are added at a temperature between about 40° C. and about 150° C., at a pressure between about 20 psi and about 300 psi, and at a $H_2/CO$ ratio between about 10:90 and about 90:10 volume percent.

7. The process of claim 1 wherein the temperature is between about 50° C. and about 125° C., at a pressure between about 40 psi and about 200 psi, and at a $H_2/CO$ ratio between about 40:60 and about 60:40 volume percent.

8. The process of claim 1 wherein the alkene or substituted alkene comprises allyl alcohol, 1-hexene, or 1-octene.

9. A process for converting an alkene or substituted alkene to a product rich in aldehydes at a high linear:-branched chain aldehyde ratio, which comprises contacting the alkene or substituted alkene, in the presence of carbon monoxide and hydrogen at conditions conducive to hydroformylation, with a composition comprising:

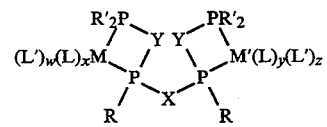

(I)

wherein

M is a Group VIII metal;

M' is a Group VIII metal;

X is selected from the group consisting of methylene; substituted methylene CSS' where S and S' can be the same or different, and each of S and S' is a hydrocarbon moiety which can be saturated or unsaturated and which contains up to 20 carbon atoms; oxygen; and NQ where Q is a hydrocarbon moiety which can be saturated or unsaturated and which contains up to 20 carbon atoms;

each Y is selected from the group consisting of ethyl; propyl; and meta-substituted aryl having hydrogen, F, or methyl substituents; where the Ys may be the same or different;

each R is a hydrocarbon moiety which can be saturated or unsaturated and which contains up to 20 carbon atoms; where the Rs may be the same or different;

each R' is selected from the group consisting of methyl, ethyl, n-propyl, n-butyl, methoxy, ethoxy, propoxy, and butoxy; where the R's may be the same or different;

each L and L' is a substituent ligand selected from the group consisting of H, CO, alkenyl, alkyl, substituted alkenyl, and substituted alkyl; where the Ls may be the same or different; and where the L's may be the same or different; and the values of the numbers w, x, y, and z for the ligands L and L' depend on the metal centers M and M' and are selected such that each metal center M and M' has 14, 16, or 18 valence electrons.

* * * * *